(12) United States Patent
Mondala et al.

(10) Patent No.: US 9,982,393 B2
(45) Date of Patent: May 29, 2018

(54) CHITOSAN AS A BIOBASED BARRIER COATING FOR FUNCTIONAL PAPERBOARD PRODUCTS

(71) Applicant: Western Michigan University Research Foundation, Kalamazoo, MI (US)

(72) Inventors: Andro Hernandez Mondala, Kalamazoo, MI (US); Brian Richard Young, Kalamazoo, MI (US)

(73) Assignee: Western Michigan University Research Foundation, Kalamazoo, MI (US)

( * ) Notice: Subject to any disclaimer, the term of this patent is extended or adjusted under 35 U.S.C. 154(b) by 140 days.

(21) Appl. No.: 15/207,021

(22) Filed: Jul. 11, 2016

(65) Prior Publication Data
US 2017/0016182 A1    Jan. 19, 2017

Related U.S. Application Data

(60) Provisional application No. 62/192,346, filed on Jul. 14, 2015.

(51) Int. Cl.
   *B32B 29/00* (2006.01)
   *B01F 3/04* (2006.01)
   (Continued)

(52) U.S. Cl.
   CPC ............ *D21H 21/16* (2013.01); *B32B 23/06* (2013.01); *B32B 29/002* (2013.01); *B32B 29/06* (2013.01);
   (Continued)

(58) Field of Classification Search
   CPC . B01F 3/04; B32B 23/04; B32B 23/06; B32B 29/00; B32B 29/002; B32B 29/06
   (Continued)

(56) References Cited

U.S. PATENT DOCUMENTS 6,200,595 B1 * 3/2001 Motoyashiki ......... A61L 15/585
                                                        424/443
8,066,803 B2 * 11/2011 Sauer ..................... A01N 25/34
                                                        55/382

(Continued)

OTHER PUBLICATIONS

Kuusipalo, J. et al. Chitosan as a coating additive in paper and paperboard, Tappi journal, 2005, pp. 17-21, vol. 4: No. 8.

(Continued)

*Primary Examiner* — Robert A Hopkins
(74) *Attorney, Agent, or Firm* — Price Heneveld LLP

(57) ABSTRACT

This invention relates to the composition of a chitosan coated paper wherein the chitosan may be derived from a variety of sources. Methods of using chitosan as a surface coating or pulp additive to tune the properties of paper and paperboard products are also described. The chitosan applied is a bio-based and environmentally friendly barrier coating and/or additive material for the manufacture of functional paper and paperboard products, specifically as evaporative cooling media requiring wet strength and structural integrity, wicking, and moisture resistance as an alternative to conventional phenolic-based resins. The solid-state fermentation method to produce chitosan and its derivatives offer renewable bio-based materials towards the manufacture of functional paper products that are eco-friendly but also offer uncompromized performance levels.

20 Claims, 6 Drawing Sheets

(51) Int. Cl.
  *D21H 21/16* (2006.01)
  *D21H 19/24* (2006.01)
  *C12P 19/04* (2006.01)
  *F28C 3/08* (2006.01)
  *B32B 29/06* (2006.01)
  *B32B 23/06* (2006.01)
  *D21H 17/24* (2006.01)

(52) U.S. Cl.
  CPC .............. *C12P 19/04* (2013.01); *D21H 17/24* (2013.01); *D21H 19/24* (2013.01); *F28C 3/08* (2013.01)

(58) Field of Classification Search
  USPC .............................................. 428/532, 537.5
  See application file for complete search history.

(56) References Cited

U.S. PATENT DOCUMENTS

2007/0292691 A1   12/2007   Chang et al.
2013/0299109 A1   11/2013   Hietaniemi et al.

OTHER PUBLICATIONS

Kjellgren, H. et al., Barrier and surface properties of chitosan-coated greaseproof paper, Carbohydrate Polymers, 2006, pp. 453-460, vol. 65.

Bordenave, N. et al., Water and Moisture Susceptibility of Chitosan and Paper-Based Materials: Structure-Property RElationships, Journal of Agricultural Food and Chemistry, 2007, pp. 9479-9488, vol. 55, No. 23.

Fernandes, S.C.M. et al., Novel coated-paper materials based on chitosan and its derivatives, Encontro Nacional da TECNICELPA, Oct. 12-15, 2010, 8 pages.

* cited by examiner

CHITOSAN AS A BIOBASED BARRIER COATING FOR FUNCTIONAL PAPERBOARD PRODUCTS

FIELD OF THE INVENTION

The present invention generally relates to the composition of chitosan coated paper and paperboard products and the method of using chitosan as a surface coating or pulp additive to enhance the properties of paper and paperboard products. The invention further relates to the methods of deriving unique chitosan compositions from chitin and a chitosan-containing fungal biomass.

BACKGROUND OF THE INVENTION

Chitosan is a highly versatile biopolymer commonly derived from crustacean (i.e., crabs, shrimps, etc.) shell chitin, but is also found in the cell walls of certain fungi. It has found numerous applications in various industries due to its unique molecular characteristics as well as its ability to form fibers, films, hydrogels, and coatings, all with antimicrobial properties. Additionally, as a polymeric material of biological origin, chitosan is biodegradable, biocompatible, and has low toxicity. The molecules below show the respective structures for chitosan, chitin, and cellulose.

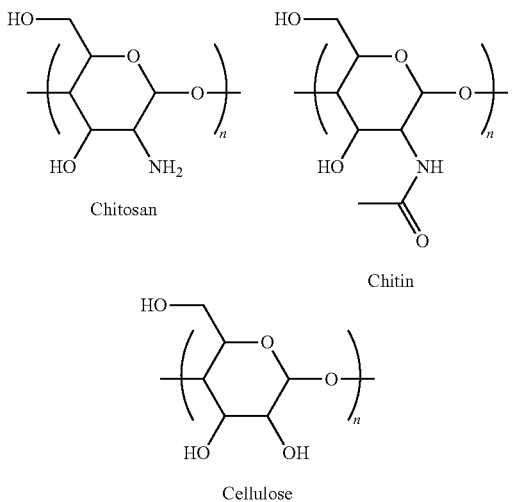

Paper is a fibrous, hydrophilic substrate; it can absorb liquid penetrants such as water, grease, and oil. Furthermore, uncoated paper allows for the easy passage of moisture. The main reason for this easy passage of moisture is the spaces between the interwoven fibers of paper that consist of countless air voids. It is these air voids and micropores within the cell walls of fibers that determine the porosity of the paper, which in turn is influenced by fiber refining.

Barrier coatings are applied to the surface of paper to decrease the porosity of the paper by filling the air voids between the fibers, coating the micropores in the fiber walls, and changing the surface chemistry of the fibers to make them resistant to fluid wetting and liquid absorption. Barrier coatings that provide rigidity and water resistance in corrugated board and paperboard products are widely used in food packaging and HVAC (Heating, Ventilation, and Air Conditioning) cooling pads for agricultural markets.

For agricultural applications, one major market is the use of barrier-coated board as part of the evaporative cooling system in barns. For these applications, water resistance and rigidity is obtained through the application of extruded polyethylene, wax, phenolic resins, or acrylic resins. The type of chemistry used depends on the degree of water resistance needed and the specific regulatory requirements that must be met. Furthermore, for HVAC, including agricultural applications, a certain degree of water absorption/wicking is required in order to produce an evaporative cooling effect on the surface of the cooling pads. This market currently consumes 4.8 M tons/yr of barrier-coated board. Phenolic resins provide stiffness to the wet paper substrate and represent 13-15% of barrier coating applications, which is estimated to be 0.6-0.7 million tons annually. However, current phenolic resin-based coatings fail quickly and their use precludes recycle of the paperboard. Therefore, there is an opportunity for natural biopolymers, with none of the VOC (volatile organic compound) and recyclability concerns that phenolic polymers have, to displace these materials along with petroleum-based barrier coating chemistries as an environmentally friendly alternative while at the same time providing enhanced structural integrity.

Although the availability of chitin/chitosan in the biosphere is estimated at 10 trillion tons, mostly from crustacean shells, only a minute fraction—2000 tons annually—is currently utilized, mostly for high purity applications in food, pharmaceutical, and biomedical products mainly due to high costs of up to $1000/kg due to processing and recovery difficulties. These current methods to generate chitin/chitosan generate significant quantities of wastes, and suffer from raw material supply interruptions, and product quality and yield inconsistencies.

The potential benefits of using chitosan-based coatings may be significant based on the renewability of this biopolymer in addition to the relative amounts of the material required for a desired application. If the demand for chitosan becomes necessary, soybean oil fatty acids and other lower cost bio-based chemistries such as lignin sulfonates could be used to supplement and produce more chitosan. Using these types of naturally occurring sources to produce chitosan could potentially further reduce costs of using chitosan by enabling more application at a competitive price.

There accordingly remains a need to find both a consistent and efficient bio-based, environmentally friendly alternative to phenolic resins for use as coatings and/or additives to paper. There also remains a need for an antimicrobial coating and/or additive to be used in paper-based evaporative cooling media while offering beneficial functional properties such as wicking ability, moisture resistance, abrasion resistance, and durability/mechanical stability in saturated conditions. Further, any bio-based materials used in these applications should be able to be reprocessed to separate and recover the coating materials and paper to recycle the resulting products for other applications.

SUMMARY OF THE INVENTION

According to one aspect of the present disclosure, a composite fiber stock material includes at least one layer of a fibrous base sheet and at least one chitosan layer having a chitosan coat weight from about 1 g/m² to about 10 g/m². The composite fiber stock material has an air permeance from about 20 nm/Pa s to about 50 nm/Pa s.

According to another aspect of the present disclosure, an evaporative cooling pad includes at least one layer of a fibrous base sheet and at least one chitosan layer having a chitosan coat weight from about 1 g/m² to about 10 g/m². The evaporative cooling pad has an air permeance from about 20 nm/Pa s to about 50 nm/Pa s.

According to still another aspect of the present disclosure, a method for making a composite fiber stock material includes forming at least one layer of a fiber stock, coupling at least one chitosan layer to the at least one layer of fiber stock using a chitosan solution including a methanol solvent and an acetic acid solvent to produce a composite fiber stock material having a chitosan coat weight with a chitosan thickness, and drying the composite fiber stock material at a controlled pressure and a controlled temperature for a period of time. The composite fiber stock material has a chitosan coat weight from about 1 g/m² to about 10 g/m² and an air permeance from about 20 nm/Pa s to about 50 nm/Pa s.

These and other aspects, objects, and features of the present disclosure will be understood and appreciated by those skilled in the art upon studying the following specification, claims, and appended drawings.

DETAILED DESCRIPTION OF THE INVENTION

Figure 1:
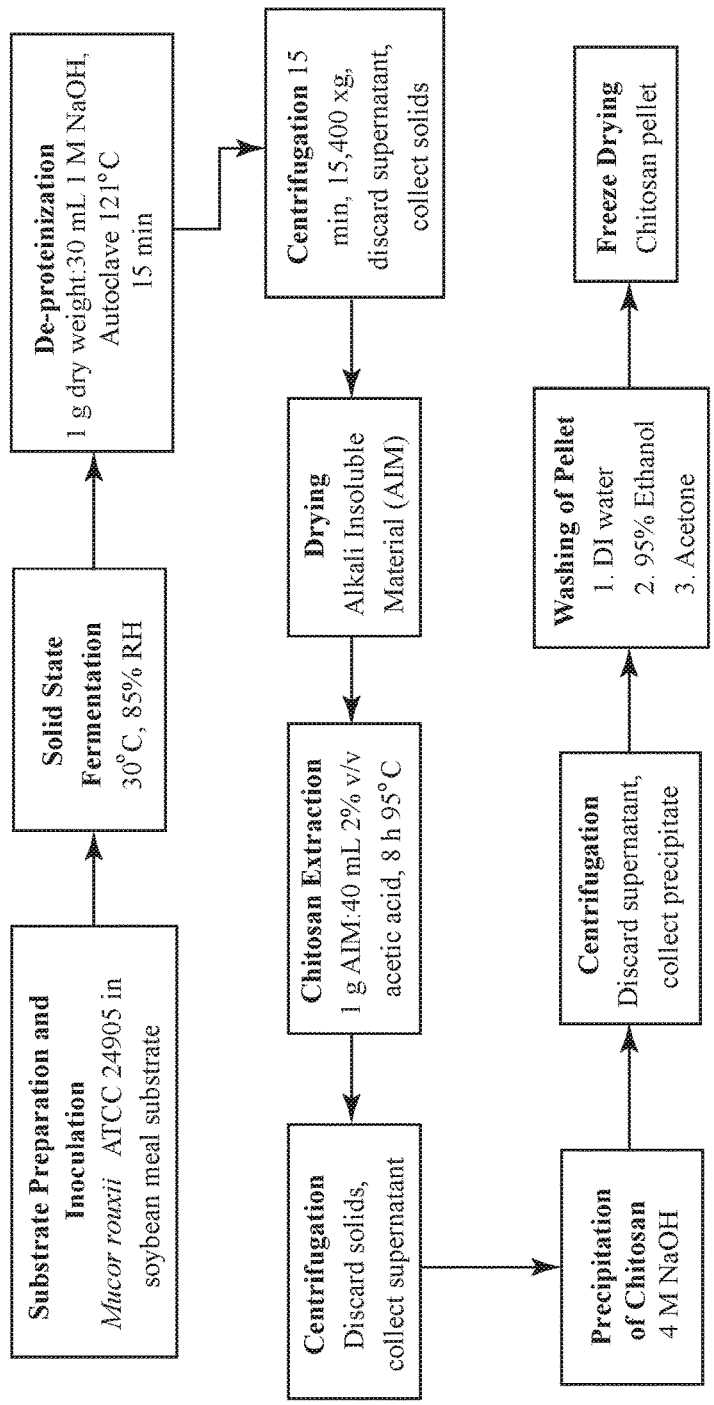
FIG. 1 is a flow chart outlining the methodology for production of fungal chitosan from solid-state fermentation.

This invention teaches the composition of chitosan coated paper and paperboard products and the method of using chitosan as a surface coating or pulp additive to enhance the properties of paper and paperboard products. This invention additionally teaches methods of deriving unique chitosan compositions from chitin and chitosan-containing fungal biomass.

The ability to use chitosan as a coating to improve the wet stiffness, wicking, and water absorption properties of a fibrous material such as paper or a paperboard product while still maintaining the fibrous material's porosity for air flow is disclosed herein. By improving the wet stiffness, wicking, and water absorption properties one can increase the useful lifespan of coated paper or a fibrous base sheet, especially for evaporative cooling pad applications. By varying the chitosan coat weight on a fibrous material, the critical-to-quality (CTQ) parameters (wet stiffness and water absorption) can be tuned for a variety of different applications. The disclosure herein additionally teaches how to produce chitosan from fungal solid-state fermentation (SSF) in soybean meal as a more cost-efficient and environmentally friendly option due to its consistent yield, controllable product quality, and milder extraction and recovery process conditions. This SSF involves the direct cultivation of fungi on a moist solid-phase nutrient medium for growth and metabolic functions to yield a unique chitosan material.

Chitosan Production and Properties

It has been surprisingly discovered that the biopolymer chitosan can be efficiently produced via fungal solid-state fermentation (SSF) of soybean residues such as soybean meal and soybean hull. The chitosan produced from this SSF process can be applied on paper or paperboard by itself or supplemented with other potential additives such as soybean oil fatty acids or lignin sulfonates to impart enhanced functionalities such as water resistance, wet structural rigidity, and wicking ability. The chitosan soy-based-derived biopolymers disclosed herein are developed from soybean meal and solid waste products of soy processing and it is anticipated that they can be used in many applications. In some embodiments, the chitosan or polymer-coated paperboard can be used as an evaporative cooling medium for air conditioning of poultry and livestock enclosures.

Chitosan can be considered a cellulose derivative because the only difference in their structures is the group attached to the C2 atom. In this position, cellulose has a hydroxyl group, whereas chitosan has an amino group or an acetoamido group. The molecules below show the respective structures for chitosan, chitin, and cellulose.

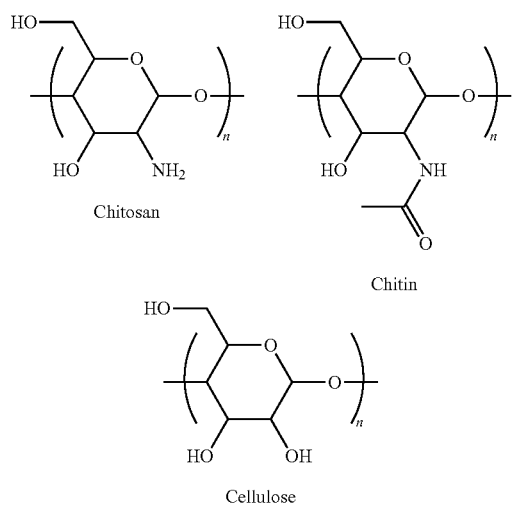

The ratio for acetamido groups to amino groups in the chain is important and is called the "degree of deacetylation." When deacetylation is less than 50%, the term "chitin" is used and when deacetylation exceeds 50%, the term "chitosan" is used. Chemically, chitosan is classified as a polycationic polysaccharide. It is easy to make membranes out of chitosan by dissolving them in an aqueous solution of an organic acid, like acetic acid, and then evaporating the solvent. The strength of the solution depends on the acid used, or more precisely on its pKa value (defined as the negative logarithm of the acid dissociation constant $K_a$) and the concentration of the chitosan in the solution. In general, chitosan dissolves when the pH of the solution decreases below 6.5 as the amino groups protonize.

When solutions are made with different amounts of chitosan, it is beneficial to use equivalent molar amounts of acid and chitosan. That way, the effect of the acid is limited to the solubilization of the chitosan. Residual acid can be washed away with 1M NaOH, and the residual NaOH can be washed away with distilled water. Monitoring the solution's pH can control the removal of residual alkali and produce flexible, transparent, homogeneous films. Because of the chitosan's chemical nature, the films are completely biodegradable and nontoxic. The chitosan will decompose to oligosaccharides without producing harmful toxic substances.

Chitin may be extracted from the bodies of fungal cells by subjecting the contents of fungi cells to chemical treatment. To minimize contamination of the chitin or chitosan end product, the sample is subjected to a series of extractions, each designed to remove impurities having different properties. These extractions may include, but are not limited to, an alkali extraction, a lipid extraction, and a hot water treatment.

Alkali extraction involves treating the samples with a solution of sufficiently high pH so as to degrade and solubilize the protein content of the sample. According to this method, the alkali treated sample is centrifuged at 15400×G for 15 minutes and the pellet neutralized and retained for chitin isolation. In some embodiments the alkali treatment is performed with NaOH. In other embodiments, the alkali extraction is performed in a solution having a final concentration of 2.5% to 10% NaOH. In yet other embodiments, the final concentration of the alkali extraction solution is 5% NaOH. The temperature and time parameters of the alkali extraction will differ according to the concentration of the alkali used in the extraction and may be routinely optimized. Routine modifications of the alkali extraction technique described herein are within the scope of the invention.

Lipid extraction may be performed on a fungal cell sample with organic solvents or other solutions routinely used for such a purpose, such as, detergents. According to this method, the solution containing the solubilized lipid is separated from chitin using routine techniques such as centrifugation. In some embodiments, lipid containing solution is separated from chitin or chitosan by centrifuging the sample at 15400×G for 15 minutes and discarding the supernatant. In some embodiments, lipid extraction is performed with an organic solvent. In other embodiments, lipid extraction is performed with methanol.

Hot water extraction may also be performed on the fungal cells sample to remove contaminants that are soluble in water at elevated temperatures. According to this method, the insoluble contaminant is separated from the chitin containing solution using techniques such as phase separation or centrifugation. In some embodiments, the heat treated sample is centrifuged at 15400×G for 15 minutes and the supernatant is retained for chitin isolation. In some embodiments, the treatment occurs at water temperatures of 50° C. to 65° C. In other embodiments, hot water treatment occurs at about 60° C.

Procedures for culturing fungi in a liquid media are well known in the art. For example, YM agar can be inoculated with a fungus, and the inoculated agar incubated at 25° C. to 37° C. for 3 to 6 days. Spores obtained from the fungus are suspended in liquid to achieve a $10^4$ to $10^7$ cfu/ml stock. This stock is directly inoculated into a fermentation medium. The fermentation medium can have an initial pH ranging from 3 to 8 and can contain 10 to 100 g/L of a carbon source (e.g., glucose, sucrose, corn starch, molasses, or soybean oil), 5 to 60 g/L of a nitrogen source (e.g., soybean meal, peptone, or corn steep liquor), 0.5 to 20 g/L of yeast extract, 0.01 to 30 g/L $(NH_4)_2SO_4$, 0 to 3 g/L $K_2HPO_4$, 0 to 3 g/L NaCl, 0 to 15 g/L $MgSO_4.7H_2O$, and/or 0 to 0.3 g/L $CaCl_2$. The fungus is grown in the fermentation medium for an additional 2 to 4 days.

The term "chitin polymer", as used herein, refers to a polymer made of at least 3 monomeric repeating units of β(1,4)-N-acetyl-(D)-glucosamine, and in some embodiments more than 10, and in even other embodiments more than 20 monomeric units. Chitin polymers are chains of monomeric β(1,4-N-acetyl-(D)-glucosamine units linked through a covalent β(1-4) osidic bond.

Chitin can be obtained from non-animal biomass, in particular from the cell walls of fungal mycelium or yeasts from several groups, including Zygomycetes, Basidiomycetes, Ascomycetes and Deuteromycetes and/or mixtures thereof, and in some embodiments Ascomycetes. *Aspergillus* and yeasts like *Saccharomyces* belong to the latter group. In some embodiments, the biomass comprises filamentous fungi or yeasts such as Aspergillium, *Penicillium, Trichoderma, Saccharomyces*, and *Schizosaccharomyces* species, and edible mushrooms such as *Agaricus, Pleurotus, Boletus*, and *Lentinula* species, and/or mixtures thereof. A common feature of these fungi and yeasts is the presence of chitin in their cell walls. In other embodiments, the said biomass is obtained from *Aspergillus niger*.

The compositions of the invention are characterized by their combination of high deacetylation levels and high molecular weights. Compositions of the invention can have deacetylation levels greater than about 50%, about 55%, about 60%, about 65%, about 70%, about 75%, about 80%, about 85%, about 90%, or about 95%. Similarly, compositions of the chitosan invention can have number average molecular weights greater than about 50,000, about 60,000, about 70,000, about 80,000, about 90,000, about 100,000, about 150,000, and/or 175,000 g/mol. In some embodiments, the chitosan invention can have number average molecular weights from about 50,000 to about 225,000, about 50,000 to about 100,000, about 70,000 to about 150,000, about 70,000 to about 100,000, and about 60,000 to about 90,000 g/mol.

Chitosan can additionally be characterized by its purity level. For example, fungal chitosan compositions used in the embodiments herein can have purity levels of greater than 75%, 80%, 85%, 90%, and 95%. In other embodiments, chitosan derived from other sources such as crustaceans can also have these same purity levels.

Soybean processing residues are excellent options for use as fermentation media for the growth of fungi that could produce chitosan due to their abundance and high nutrient content. For example, processing of one bushel (60 lbs) of soybeans would yield approximately 11 lbs of soybean oil, 48 lbs of meal, and 1 lb of other residues such as the hulls and mill runs. Soy meal is ground soybean cakes, flakes or chips produced after cracking, heating, and flaking of dehulled soybeans and after extraction to separate the soybean oils from the cake using hydrocarbon solvents such as hexane. Soy meal has a high protein content of about 44-49% by weight, along with about 40% carbohydrates, about 12% moisture, and about 0.5-1% residual oil. Soybean hulls and mill runs consist primarily of the seed coat of soybeans obtained after cleaning, cracking, and aspirating the beans and contain around about 35% carbohydrates, about 35% fiber, about 12% protein, about 9-13% moisture, and about 1% residual oils. These characteristics make soybean meal, soybean hulls, and mill runs ideal solid-state fermentation (SSF) substrates for the growth and cultivation of fungi that can be used to produce chitosan. The conventional use of the residues includes supplementation of high protein soybean meal for animal feed; however such use is limited due to the presence of oligosaccharides that are indigestible by non-ruminant livestock and poultry. On the other hand, certain fungi could utilize a variety of enzymes to degrade oligosaccharides and protein and utilize these carbon and nitrogen sources for growth and biosynthesis of chitosan in a cost-effective manner via solid-state fermentation. At the same time, the resulting fermented residues could be recovered and reused in subsequent fermentations or as high protein feed supplements after separation of the chitosan-containing fungal biomass.

To use solid-state fermentation using soy meal, a mixture of soy meal and soy hulls can be used as a fermentation media. In some embodiments, the amount of meal can be greater than 50%, greater than 60%, greater than 70%, greater than 80%, greater than 90%, or can be 100%. The amount of soybean hulls can be added to the soybean meal to make up the remainder of the fermentation media. The lower protein content in the soybean hulls may result in reduced fungal biomass growth and chitosan yield. In some embodiments, additional nutrients or other crop meals can be used with or in substitute of the soy meal and/or soy hulls. For example, the fermentation media can comprise sugar beet meal, corn meals, soup bean meal, navy bean meal, and/or potato meal.

The methodology of performing production of fungal chitosan from solid-state fermentation begins with substrate preparation and inoculation, then solid-state fermentation, then de-proteinization, followed by centrifugation, drying, with chitosan extraction next, then centrifugation, precipitation of chitosan, centrifugation, washing of pellet, and lastly freeze drying. This general methodology is summarized in FIG. 1 although some steps may be added, altered, or removed depending on the application in other embodiments. For example, in some embodiments, the chitosan or chitosan pellet may be dried using freezer drying, air drying, spray drying, and/or drum drying techniques.

Figure 2:
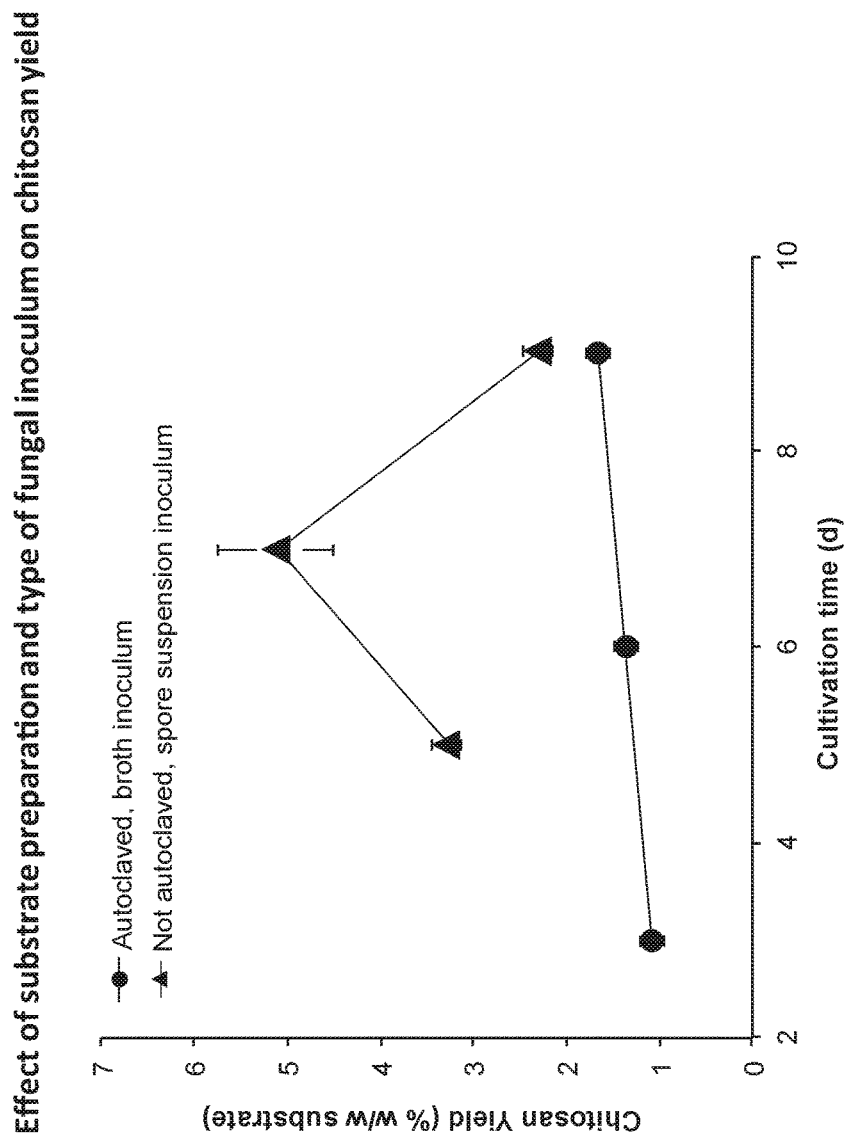
FIG. 2 is a graph illustrating the effect of substrate preparation and type of fungal inoculum on chitosan yield.

The effect of substrate preparation and the type of fungal inoculum can have an effect on the chitin and chitosan yield. For example, pre-autoclaving soy meal substrate led to reduced fungal growth and chitosan yield. Aqueous spore suspension was found to be preferable over fungal broth for higher growth and chitosan yield. Lastly, a maximum yield was found around seven days for the non-autoclaved substrate as shown in FIG. 2. The amount of moisture in the substrate was also shown to have an effect on the fermentation process. It was found that the lower moisture content can provide higher substrate porosity for ease of oxygen transport in the matrix.

In summary, fungal chitosan could be produced by solid-state fermentation of soy meal substrate wherein higher fungal biomass growth and chitosan production yields are obtained when using non-autoclaved soy meal substrate and fungal spore suspension versus fungal culture broth which could be a possible effect of morphological transitions.

Chitosan Film Preparation

The source of chitosan for the preparation of films in this invention is not meant to be limiting. Chitosan derived from any chitin-containing biological source is suitable for the preparation of the films taught herein, for example, chitosan can be derived from a biomass selected from the group consisting of: crustaceans, insects, mollusks, and fungi. In some embodiments, the chitosan can be derived from fungi. In other embodiments, the chitosan can be derived from marine organisms. In yet other embodiments, the chitosan can be derived from insects.

The use of chitosan as a coating requires less coating weight than that needed for phenolic resins to import enhanced functional characteristics on paper, at roughly one fourth the cost of phenolic resins with less coating weight. The use of chitosan as a coating and/or additive for fibrous base sheets offers numerous cost and property advantages over the traditionally used phenolic resins.

At least one layer of chitosan can be added or coupled to any paper or fibrous base sheet. Some non-limiting examples of paper and fibrous base sheets are dry paper, wet paper, pre-made dry paper, pre-made paper, dry fibrous base sheets, wet fibrous wet sheets, fibrous cellulose based materials, dry cellulose based materials, wet fibrous cellulose based materials, fibrous cellulose based sheets, dry cellulose based sheets, wet fibrous cellulose based sheets, fiber stock, or a combination thereof. The paper and/or fibrous base sheet materials can be pre-made before the addition of chitosan or can be made in a process wherein the chitosan is added as a step in the paper making process. The terms paper and fibrous base sheet can be used interchangeably to represent the same scope of materials. In some embodiments, the chitosan is added through at least one layer to a pre-made dry paper, pre-made dry fibrous base sheet, or a combination thereof. In other embodiments, at least one layer of chitosan is added to a paper fibrous base sheet, or a combination thereof.

The term "composite fiber stock material", as used herein, refers to the material made when at least one layer of chitosan is added or otherwise coupled to any paper or fibrous base sheet. Coating paper with one or more layers of chitosan can have numerous effects on the properties of the paper. For example, a chitosan coating can have a reinforcing effect on the cross and machine directions, it can influence the optical properties, it can vary the adhesion properties, and it can change the porosity of the paper to both air and oxygen flow.

The amount of chitosan added to the paper is measured as the coat weight ($g/m^2$) and can be varied depending on the desired properties and the number of layers added. The coat weight of chitosan can be from an amount greater than 0 $g/m^2$ to about 10 $g/m^2$, from about 1 $g/m^2$ to about 10 $g/m^2$, from about 1 $g/m^2$ to about 9 $g/m^2$, from about 2 $g/m^2$ to about 8 $g/m^2$, from about 3 $g/m^2$ to about $7/m^2$, from about 4 $g/m^2$ to about 6 $g/m^2$, from about 2 $g/m^2$ to about 7 $g/m^2$, from about 3 $g/m^2$ to about 6 $g/m^2$, from about 3 $g/m^2$ to about 5 $g/m^2$, from about 3 $g/m^2$ to about 4 $g/m^2$, from about 1 $g/m^2$ to about 5 $g/m^2$, from about 1 $g/m^2$ to about 4 $g/m^2$, from about 5 $g/m^2$ to about 10 $g/m^2$, from about 6 $g/m^2$ to about 10 $g/m^2$, and about 1 $g/m^2$, about 1.5 $g/m^2$, about 2 $g/m^2$, about 2.5 $g/m^2$, about 3 $g/m^2$, about 3.5 $g/m^2$, about 4 $g/m^2$, about 4.5 $g/m^2$, about 5 $g/m^2$, about 5.5 $g/m^2$, about 6 $g/m^2$, about 6.5 $g/m^2$, about 7 $g/m^2$, about 7.5 $g/m^2$, about 8 $g/m^2$, about 8.5 $g/m^2$, about 9 $g/m^2$, about 9.5 $g/m^2$, and about 10 $g/m^2$.

In addition to the amount of chitosan added to the paper, the thickness of the added chitosan film can also be used to describe the addition. The thickness of the chitosan film is measured in μm and can vary from about 5 μm to about 75 μm, from about 10 μm to about 50 μm, from about 10 μm to about 40 μm, from about 10 μm to about 30 μm, from about 15 μm to about 35 μm, from about 15 μm to about 30 μm, from about 15 μm to about 25 μm, from about 20 μm to about 30 μm, and from about 20 μm to about 25 μm. In some embodiments, at least one chitosan layer is coupled to the fibrous base sheet. In other embodiments, one layer is coupled to the fibrous base sheet. In still other embodiments, two layers, three layers, or four layers are coupled to the fibrous base sheet.

Chitosan can be added to paper on either one side or both sides of the paper utilizing one or more layers or applications of chitosan. In some embodiments, the chitosan film is added as a single layer film to only one side of the paper. In other embodiments, the chitosan film is added as a single layer film to both sides of the paper. The chitosan films of the current invention are meant to balance the appropriate amount of chitosan to be added to a paper product to improve the properties of the paper while not clogging the pores of the paper. The use of chitosan in the prior art clogs the pores of the paper by applying large quantities of chitosan to the paper, thus reducing the air permeance of the paper, while enhancing other desired properties.

The air permeance (AP) is the degree in which a material or paper admits a flow of air. The air permeance of the inventive chitosan coated paper can be from about 1 nm/Pa s to about 100 nm/Pa s, from about 10 nm/Pa s to about 50 nm/Pa s, from about 20 nm/Pa s to about 50 nm/Pa s, from about 30 nm/Pa s to about 50 nm/Pa s, from about 20 nm/Pa s to about 40 nm/Pa s, or from about 25 nm/Pa s to about 35 nm/Pa s. In other embodiments, the air permeance of the inventive chitosan coated paper can be about 20 nm/Pa s, about 25 nm/Pa s, about 30 nm/Pa s, about 35 nm/Pa s, about 40 nm/Pa s, about 45 nm/Pa s, or about 50 nm/Pa s.

The Cobb value indicates whether paper, paperboard, corrugated fiber board, or a chitosan coated paper has the ability to absorb water. The Cobb values vary depending on the paper used and the coat weight of the chitosan. The Cobb values of a chitosan coated paper can from about 10 $g/m^2$ to about 75 $g/m^2$, from about 20 $g/m^2$ to about 60 $g/m^2$, from about 20 $g/m^2$ to about 40 $g/m^2$, from about 20 $g/m^2$ to about 30 $g/m^2$, from about 25 $g/m^2$ to about 35 $g/m^2$, and from about 20 $g/m^2$ to about 25 $g/m^2$.

The wet stiffness of paper can be about 1.0 gram-force, can be about 1.1 gram-force, can be about 1.2 gram-force, can be about 1.3 gram-force, can be about 1.4 gram-force, can be about 1.5 gram-force, can be about 1.6 gram-force, can be about 1.7 gram-force, can be about 1.8 gram-force, can be about 1.9 gram-force, can be about 2.0 gram-force, can be from about 1.0 gram-force to about 2.0 gram-force, can be from about 1.1 gram-force to about 1.9 gram-force, can be from about 1.2 gram-force to about 1.8 gram-force, can be from about 1.3 gram-force to about 1.7 gram-force, and can be from about 1.4 gram-force to about 1.6 gram-force.

The wicking height under standard TAPPI conditions can be about 1 inch, can be about 2 inches, can be about 3 inches, can be about 4 inches, can be about 5 inches, can be from about 1 to about 5 inches, can be from about 1.5 to about 2.5 inches, can be from about 1.25 to about 2.25 inches, or can be from about 2 inches to about 4 inches.

The chitosan can be applied to paper and/or fibrous base sheets using a Meyer Rod Coating system using varying concentrations of chitosan in acetic acid to give a composite fiber stock material with a desired coat weight and thickness. The sheets can then be dried using steam drying at a controlled pressure and temperature for a specific amount of time. The wicking height can be adjusted through these parameters, in addition to the dry and wet Taber stiffness.

The chitosan can be utilized and/or applied using a variety of different carrier solvents. The carrier comprises water, acetic acid, methanol, ethanol, propanol, isopropanol, acetone, formic acid, or a combination thereof. In some embodiments, the carrier is water and acetic acid. In other embodiments, the carrier is methanol and acetic acid. By using a carrier of methanol and acetic acid, the resultant chitosan coating can be dried with low heat, thus saving time and lowering cost. In some embodiments, a chitosan solution to be applied to the fibrous base sheet can be made from a methanol solvent and an acetic acid solvent having a 4:1, 3:1, 2:1, 1:1, 1:2, 1:3, or 1:4 methanol to acetic acid volume ratio.

The chitosan coated sheets and/or paper can show a range of different water absorption mass gains. The water absorption of a chitosan coated paper or fibrous material can be about 30%, can be about 40%, can be about 50%, can be about 60%, and can be about 70%.

Figure 3:
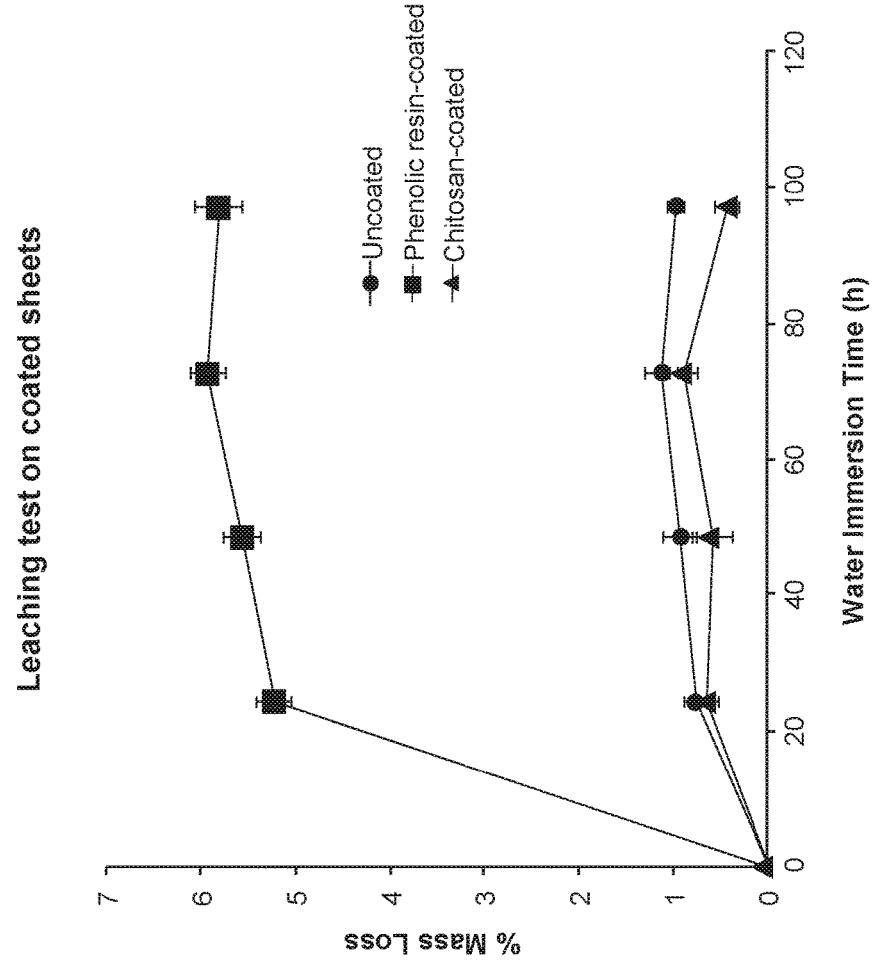
FIG. 3 is a graph illustrating the leaching of phenolic and chitosan coatings from sheets.
Figure 4:
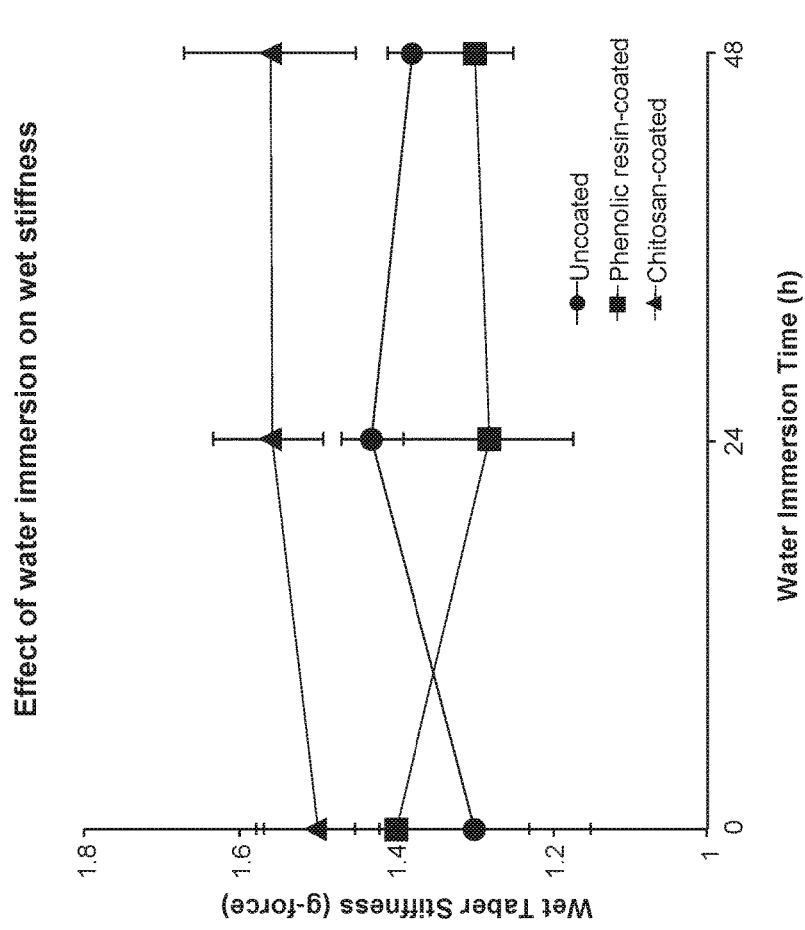
FIG. 4 is a graph illustrating the effect of water immersion on wet stiffness.

The chitosan coated paper and/or fibrous base sheets forms a composite fiber stock material that demonstrates improved stability over the phenolic coated paper. FIG. 3 shows the leaching effect of water on the respective resin coatings and FIG. 4 presents the effect of water immersion on wet stiffness. The results in FIG. 3 demonstrate that prolonged water immersion removes the phenolic coating but not the chitosan coating from paper sheets. The chitosan water stability explains the effect of water immersion on wet stiffness shown in FIG. 4. Initially, the wet stiffness for the chitosan coated paper was approximately the same as for phenolic resin coated paper, but after 2 days of immersion, the wet stiffness for the chitosan coating remained high while the wet stiffness of the phenolic resin coated paper decreased significantly. The test conditions used to generate the results in FIG. 4, simulated actual conditions for evaporative cooling pads constructed with chitosan-coated base sheets. Both of these Figures demonstrate that using chitosan as a paper coating improves the resiliency of the coated paper over extended periods of time. The percent mass loss of chitosan on a chitosan coated paper after 100 hours can be less than about 3%, less than about 2%, less than about 1%, less than about 0.5%, or can be from about 0.1% to about 3%, from about 0.1% to about 2%, or from about 0.1% to about 1%. The percent change in the wet Taber stiffness (g-force) in a chitosan coated paper after exposure to water for 24 to 48 hours can be increased about 20%, increased about 15%, increased about 10%, increased about 5%, or can be increased from about 5% to about 20%, increased from about 5% to about 15%, or increased from about 5% to about 10%.

In some embodiments, chitosan can be applied as at least one layer to paper and/or a fibrous base sheet as a chitosan solution using any suitable means. In this type of embodiment, the solution is obtained by dissolving the polysaccharide in powder form into a solvent, typically water. In other embodiments, the chitosan solution is free from discrete chitosan particles. The chitosan solution may comprise just itself, one polysaccharide, or it may comprise a mixture of different polysaccharides, for example a mixture of two or three polysaccharides. Polysaccharides can comprise water soluble cellulose derivatives, galactomannans, guar gum, locust bean gum, galactoglucomannans, carboxymethyl cellulose, xylan and substituted glycans, xyloglucans, hydrocolloids, tamarind gum, or a combination thereof. Thus, according to some embodiments a mixture of different polysaccharides may be applied to the fiber stock after it is made. Typically the concentration of the polysaccharide(s) in the chitosan solution can be less than about 60 weight %, less than about 50 weight %, less than about 40 weight %, less than about 30 weight %, less than about 20 weight %, less than about 10 weight %, less than about 5 weight %, from about 0.02 weight % to about 5 weight %, from about 0.05 weight % to about 3 weight %, or from about 0.05 weight % to about 2 weight %. The concentration of polysaccharides with a high degree of polymerization (DP) in the solution may be <1 weight %, 0.05-1 weight %, or 0.2-0.6 weight %.

In other embodiments of the invention, the chitosan can be applied as one or more layers onto the paper and/or fibrous base sheets together with a retention or drainage agent. The retention or drainage agent may be any suitable retention agent. Retention agents comprise anionic or cationic polyacrylamides, polyvinylamine, polyethyleneimine, cationic starch, bentonite or silica. In some embodiments, the retention agent may be anionic or cationic polyacrylamide, polyvinylamine or polyethyleneimine. The retention agent and the chitosan may be added as separate solutions, or they may be added as single solution, comprising both the retention agent and the chitosan. The polymeric retention agent dosage may be 50-1000 g/t, in some embodiments 100-600 g/t, given as dry polymer, and in some embodiments the polysaccharide dosage may be 200-4000 g/t, in other embodiments 500-2500 g/t, given as dry polymer.

In some embodiments of the invention the at least one chitosan layer is applied onto the paper and/or fibrous base sheets together with an anionic, cationic or amphoteric dry strength agent. The dry strength agent comprises polyacrylamides, glyoxylated polyacrylamides, polyvinylamines, polyamine epichlorohydrin co-polymers (PAAE), starch derivatives, carboxymethyl cellulose, or a combination thereof. The dry strength agent may be applied in an amount of 0.1-4 kg/t paper, typically in an amount of 0.2-2 kg/t, given as active substance.

The chitosan can be applied as one or more layers on the paper and/or fibrous base sheets by spraying, by coating, by film transfer or by foam layer application. It may be applied by using film transfer to a press belt, or by feeding the chitosan solution from a separate feed source. In some embodiments, the application of the chitosan solution is applied by spraying. It has been found that spraying the chitosan solution onto the paper and/or fibrous base sheets provides many surprising advantages. Spraying the chitosan solution allows for the polysaccharide solution to be evenly distributed on the entire surface of the paper and/or fibrous base sheets.

In some embodiments, the at least one chitosan layer is applied by spraying onto the paper and/or fibrous base sheets. It has been observed that the chitosan amount applied may be reduced when the application is done by spraying, and still the improved wet stiffness, porosity, and wicking characteristics of the paper web are obtained. A chitosan solution suitable for use as a spray may be obtained, for example, by dissolving a chitosan in powder form into water in order to form an about 0.2 weight % to about 20 weight %, or about 0.3 weight % to about 3 weight % solution.

In other embodiments, the at least one chitosan layer is applied by foam layer application or foam coating. The chitosan may be applied by foam coating, whereby the polysaccharide is applied as a foam, which has an air content of 60-95%, onto the paper and/or fibrous base sheets.

The chitosan can be applied in an amount greater than zero to about 10 kg/(ton paper), or about 0.3 to about 3 kg/(ton paper). In embodiments where the chitosan is applied by spraying, it may be applied in amounts of about ≤2 $g/m^2$, about 0.05-1.5 $g/m^2$, about ≤1 $g/m^2$, from about 0.05 to about 1 $g/m^2$, from about 0.05 to about 0.5 $g/m^2$, or from about 0.05 to about 0.3 $g/m^2$.

In other embodiments of the invention, one or more additional polysaccharides may be applied on the paper and/or fibrous base sheets after each other by spraying. Thus layers of different polysaccharides may be easily applied on top of each other in order to obtain films with desired properties.

In yet other embodiments, an anionic or cationic polymer solution may be applied to the paper and/or fibrous base sheets before or after the addition of the chitosan. For example, the application of the chitosan to the paper and/or fibrous base sheets may be preceded or followed by application of cationic or anionic polymer solution. This kind of sequential application of chitosan and one or more polymers to the paper and/or fibrous base sheets may produce a marked improvement of dry paper strength. Anionic and cationic polymer solutions may also be pre-mixed together before their application, to the paper and/or fibrous base sheets.

Figure 5:
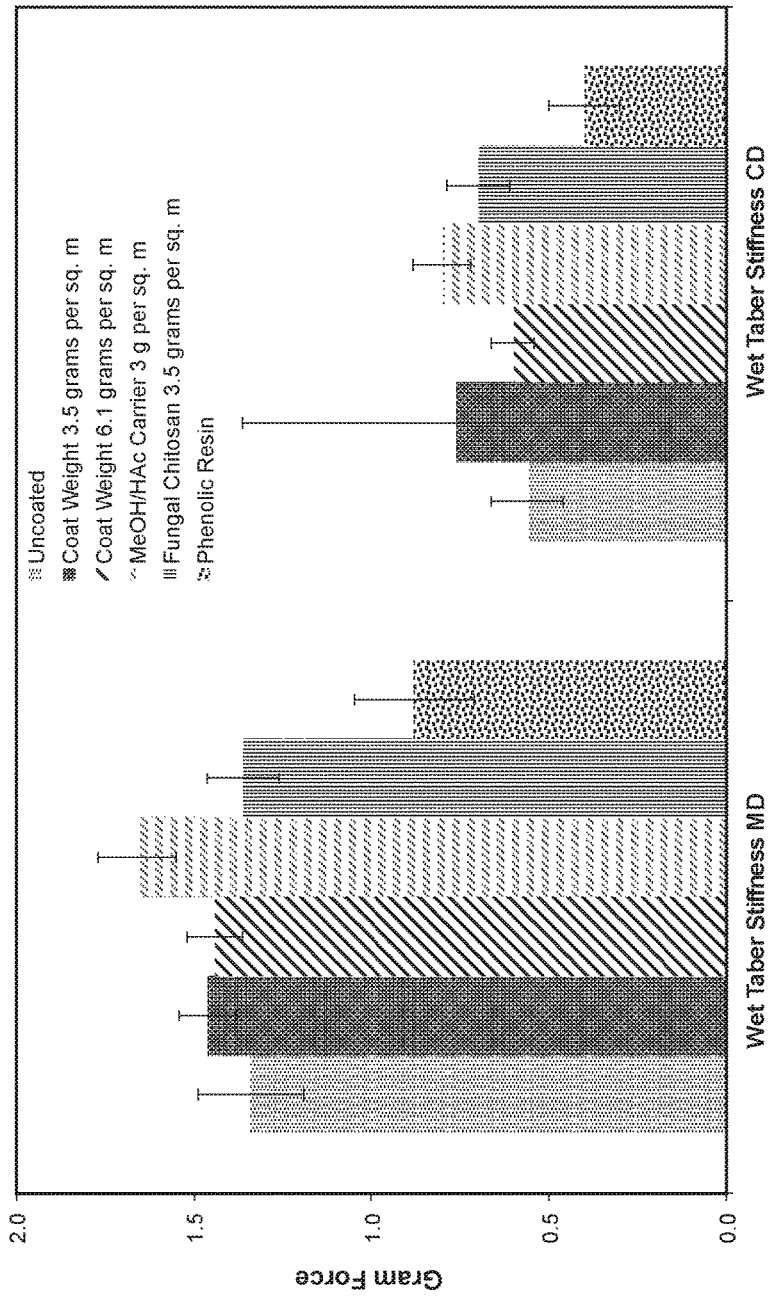
FIG. 5 is a graph illustrating the wet stiffness of coated paper base sheets at different chitosan coating conditions.
Figure 6:
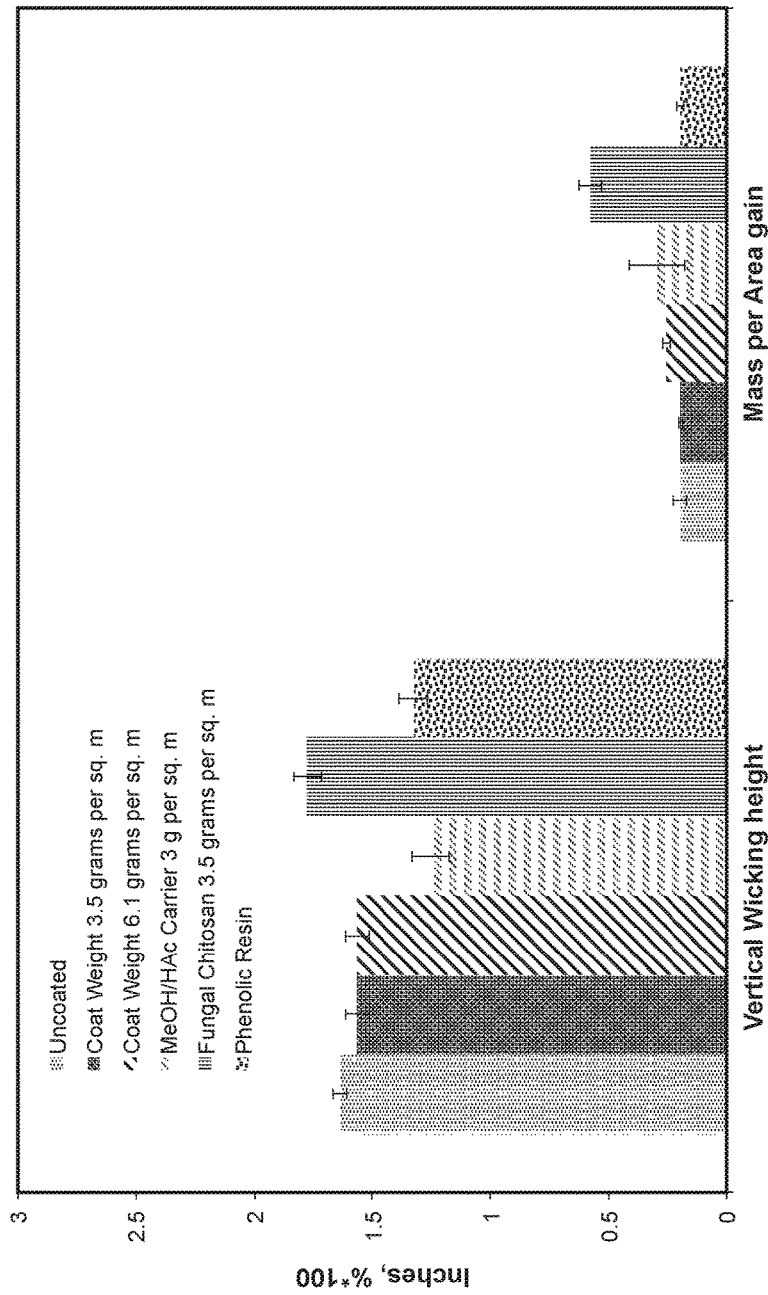
FIG. 6 is a graph illustrating the vertical wicking and water absorption of coated paper base sheets.

The results herein demonstrate the potential of using chitosan from either crustacean or fungal soybean meal solid-state fermentation sources in simultaneously improving wet stiffness and water absorption of paper base sheets used for HVAC media, in comparison to conventional phenolic resin-based coating. With phenolic resin-based coatings, wet stiffness improves with a decrease in water absorption. A chitosan carrier system useful in an industrial setting because of its low temperature volatility, acetic acid and methanol mixture, created a chitosan coated paper that was significantly stiffer when wet (FIG. 5—machine direction (MD) and the cross direction (CD)) and was comparable in water wicking and absorption (FIG. 6) to a phenolic resin coated paper. Papers coated with fungal or crustacean-derived chitosans in an acetic acid carrier all had greater wet stiffness (FIG. 5) and vertical wicking (FIG. 6) than phenolic resin based paper. These results highlight the superior critical-to-quality (CTQ) parameter levels of chitosan-coated paper base sheets. The results in FIGS. 3 and 4 demonstrate that these superior qualities of chitosan coated papers will be maintained over a greater lifetime when compared to phenolic resin coated papers. Use of a greater chitosan coat weight (from 3.5 $g/m^2$ to 6.1 $g/m^2$ coat weight) was not necessary and did not significantly improve CTQ parameter levels (FIGS. 5 and 6).

In embodiments using a HVAC apparatus, generally an evaporative cooler uses a fan to draw air through an evaporative cooling pad which provides a large surface area for the evaporation of water into air. Water may be added to the evaporative cooling pad at the top, bottom, or side of the evaporative cooling pad so the membrane can continually remain saturated with water. The water may be drawn into the HVAC apparatus and applied to the evaporative cooling pad using a water pump. The designs for evaporative coolers using evaporative cooling pads in the HVAC apparatus can vary. For example, some non-limiting embodiments for evaporative cooler designs are direct evaporative cooling, mechanical direct evaporative cooling, passive direct evaporative cooling, indirect evaporative cooling, passive indirect evaporative cooling, two-stage evaporative cooling, and combinations thereof. In other embodiments of an HVAC apparatus, the evaporative cooling pad can be used to adjust the humidity of an environment and the temperature of the environment. In the embodiments where the HVAC apparatus uses evaporative cooling pads, the evaporative cooling pad may have any of the properties disclosed herein for the composite fiber stock material, the chitosan coated paper, and/or the chitosan coated fibrous base sheets. The methods of making a composite fiber stock material disclosed herein may also be applied to making evaporative cooling pads.

In summary, using chitosan as a coating improves wet stiffness, wicking and water absorption for paper and other fibrous materials. These features can increase the useful lifespan of coated paper for evaporative cooling pads application.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

It is important to note that the construction and arrangement of the elements of the composition as shown and described in the exemplary embodiments is illustrative only. Although only a few embodiments of the present innovations have been described in detail in this disclosure, those skilled in the art who review this disclosure will readily appreciate that many modifications are possible (e.g., proportions of the various elements, values of parameters, coating arrangements, use of materials, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the nature or number of adjustment positions provided between the elements may be varied. It should be noted that the elements and/or assemblies of these fiber stock systems may be constructed from an additional wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

For the purposes of this disclosure, the term "coupled" (in all of its forms, couple, coupling, coupled, etc.) generally means the joining of two components (e.g., physical parts or mechanical) directly or indirectly to one another. Such joining may be stationary in nature or movable in nature. Such joining may be achieved with the two components (e.g., physical parts or mechanical) and any additional intermediate members being integrally formed as a single unitary body with one another or with the two components. Such joining may be permanent in nature or may be removable or releasable in nature unless otherwise stated.

It will be understood that any described processes or steps within described processes may be combined with other disclosed processes or steps to form composite fiber stock materials within the scope of the present compositions and materials. The exemplary composite fiber stock materials and processes disclosed herein are for illustrative purposes and are not to be construed as limiting.

It is also to be understood that variations and modifications can be made on the aforementioned composite fiber stock materials and methods without departing from the concepts of the present composite fiber stock materials, and further it is to be understood that such concepts are intended to be covered by the following claims unless these claims by their language expressly state otherwise.

The above description is considered that of the illustrated embodiments only. Modifications of the composite fiber stock materials will occur to those skilled in the art and to those who make or use the composite fiber stock materials. Therefore, it is understood that the embodiments shown in the drawings and described above is merely for illustrative purposes and not intended to limit the scope of the device, which is defined by the following claims as interpreted according to the principles of patent law, including the Doctrine of Equivalents.

Listing of Non-Limiting Embodiments

Embodiment A is a composite fiber stock material comprising at least one layer of a fibrous base sheet; and at least one chitosan layer comprising a chitosan coat weight from about 1 g/m$^2$ to about 10 g/m$^2$; wherein the composite fiber stock material has an air permeance from about 20 nm/Pa s to about 50 nm/Pa s.

The composite fiber stock material of Embodiment A wherein the air permeance is from about 25 nm/Pa s to about 35 nm/Pa s.

The composite fiber stock material of Embodiment A or Embodiment A with one or more of the intervening features wherein the composite has a Cobb value from about 10 g/m$^2$ to about 50 g/m$^2$.

The composite fiber stock material of Embodiment A or Embodiment A with one or more of the intervening features wherein the composite material has a wet stiffness from about 1.0 gram-force to about 2.0 gram-force.

The composite fiber stock material of Embodiment A or Embodiment A with one or more of the intervening features wherein the composite material has a wet stiffness of about 1.6 gram-force.

The composite fiber stock material of Embodiment A or Embodiment A with one or more of the intervening features wherein the composite material has a wicking height of about 2 inches.

The composite fiber stock material of Embodiment A or Embodiment A with one or more of the intervening features wherein the at least one chitosan layer is derived from a fungal biomass in a solid-state fermentation of a soybean meal.

The composite fiber stock material of Embodiment A or Embodiment A with one or more of the intervening features wherein the at least one chitosan layer is derived from a biomass selected from the group consisting of: crustaceans; insects; mollusks; and fungi.

Embodiment B is an evaporative cooling pad comprising at least one layer of a fibrous base sheet; and at least one chitosan layer comprising a chitosan coat weight from about 1 g/m$^2$ to about 10 g/m$^2$; wherein the evaporative cooling pad has an air permeance from about 20 nm/Pa s to about 50 nm/Pa s.

The evaporative cooling pad of Embodiment B wherein the evaporative cooling pad is used in a heating, ventilation, and air conditioning apparatus.

The evaporative cooling pad of Embodiment B or Embodiment B with one or more of the intervening features wherein the air permeance is from about 25 nm/Pa s to about 35 nm/Pa s.

The evaporative cooling pad of Embodiment B or Embodiment B with one or more of the intervening features wherein the composite has a Cobb value from about 10 g/m$^2$ to about 50 g/m$^2$.

The evaporative cooling pad of Embodiment B or Embodiment B with one or more of the intervening features wherein the composite material has a wet stiffness from about 1.0 gram-force to about 2.0 gram-force.

The evaporative cooling pad of Embodiment B or Embodiment B with one or more of the intervening features wherein the composite material has a wicking height of about 2 inches.

The evaporative cooling pad of Embodiment B or Embodiment B with one or more of the intervening features wherein the at least one chitosan layer is derived from a fungal biomass in a solid-state fermentation of a soybean meal.

The evaporative cooling pad of Embodiment B or Embodiment B with one or more of the intervening features wherein the at least one chitosan layer is derived from a biomass selected from the group consisting of: crustaceans; insects; mollusks; and fungi.

Embodiment C is a method for making a composite fiber stock material comprising: forming at least one layer of a fiber stock; coupling at least one chitosan layer to the at least one layer of fiber stock using a chitosan solution comprising a methanol solvent and an acetic acid solvent to produce a composite fiber stock material having a chitosan coat weight with a chitosan thickness; and drying the composite fiber stock material at a controlled pressure and a controlled temperature for a period of time; wherein the composite fiber stock material has a chitosan coat weight from about 1 $g/m^2$ to about 10 $g/m^2$ and an air permeance from about 30 nm/Pa s to about 50 nm/Pa s.

The method of Embodiment C wherein the composite fiber stock material has a Cobb value from about 10 $g/m^2$ to about 50 $g/m^2$.

The method of Embodiment C or Embodiment C with one or more of the intervening features wherein the composite fiber stock material has a wicking height of about 2 inches.

The method of Embodiment C or Embodiment C with one or more of the intervening features wherein the at least one chitosan layer is derived from a fungal biomass in a solid-state fermentation of a soybean meal.

EXAMPLES

Prophetic Example 1: Development of a Fermentation Process for Fungal Chitosan Production from Soybean Residues This will involve the development of a sustainable bioprocessing technology based on solid-state fermentation that will utilize soy-processing products as substrates for the cultivation of fungal strains producing chitosan. Soybean residues such as meal and hulls will be obtained from suppliers, characterized, and prepared for use as fermentation substrates. Bench scale solid-state fermentation (SSF) experiments will be conducted to screen and select fungal strains among those specified in literature for growth and chitosan production. The bench-scale tests will involve preparation of stock fungi cultures in agar slants, propagation of seed cultures in a liquid media in shake flasks, and inoculation of seed culture into the solid substrate—soybean meal and residues prepared by moisture and nutrient content adjustment as needed. All culture transfers will be performed aseptically under a laminar flow hood and liquid and solid cultures will be incubated in enclosed temperature and humidity-controlled incubators. After the incubation period, the fungal biomass will be inactivated during the chitosan recovery step, which will involve high-pressure hot alkaline hydrolysis followed by hot dilute acid extraction. All spent substrate and fungal biomass debris will be decontaminated by autoclaving at 121° C., 20 psig for 1 hour prior to disposal. Samples of the spent substrate will also be characterized for residual carbohydrate and protein content to determine their potential suitability as animal feed supplement. The chitosan produced will be quantified gravimetrically and characterized by Fourier Transform Infrared Spectroscopy (FTIR), Gel Permeation Chromatography, and UV Spectroscopy to complete the characterization. Operating variables of the fermentation process as well as the downstream processing steps will be optimized for maximum fungal growth and to achieve the target chitosan production yield. The fermentation process will be mathematically modeled and an economic analysis will be conducted to enable the design of pilot and commercial-scale SSF bioreactors and downstream processing equipment.

Prophetic Example 2: Application and Testing of Model Chitosan and Chitosan Derivatives as Barrier Coatings for Paperboard in Evaporative Cooling Applications This will involve laboratory coating of model chitosan and selected chitosan derivatives on Kraft base sheets used for manufacturing paperboard evaporative cooling pads. The chitosan-treated paperboard will be tested and screened for the following critical-to-quality (CTQ) parameters: vertical wicking and wet stiffness and will be compared with the standard phenolic resin-coated sheets. The vertical wicking test will be conducted by suspending 10"×1" treated paperboard strips above a trough of water with the tips partially submerged for 10 minutes under standard TAPPI (Technical Association of the Pulp and Paper Industry) conditions of 73° F. and 50% relative humidity. Wet stiffness will be tested by immersing a 2.5"×2" sample of treated paperboard in water for 1 minute followed by blotting with standard TAPPI blotting paper using a roller of known weight and testing using a Taber Stiffness tester. Microscopic, spectroscopic, and imaging techniques will also be applied to visualize the coated paperboard products and decipher structural properties at the micro-level. The results obtained herein will enable the selection of promising chitosan-based polymers for further evaluation in the specified application and compare their properties and performance with conventional phenolic resin-coated paper.

Prophetic Example 3: Pilot Production and Testing of Fungal Chitosan and Chitosan-Coated Paperboard This task will involve production of the chitosan-based biopolymer coatings and the coated-evaporative paperboard cooling medium at the pilot scale using Western Michigan University's bioprocessing, coating and converting equipment. The research team will be assisted by a manufacturer of phenolic resin-coated paperboard and an additional manufacturer who purchases these coated paperboards and manufactures evaporative cooling pads which are currently marketed and used in poultry farms for cooling of enclosures, in field trials for the chitosan-coated paperboard. These industrial partners will participate in the development work and evaluation of the chitosan-coated paperboard cooling media for potential commercialization and marketing.

Example 1: Chitosan Production Via Fungal Solid-State Fermentation of Soybean Meal As previously mentioned, this invention aims to add value to soybean meal by utilizing it as a solid-state fermentation (SSF) substrate for growth and production of the high-value biopolymer chitosan by filamentous fungi. Chitosan has numerous current and potential applications, one of them being as a barrier coating material to provide specific functionalities to paper and paperboard products. Currently, chitosan is being produced through the processing of seafood wastes (i.e., crab, shrimp, and lobster shells). These are tough and highly recalcitrant materials requiring costly and intensive processing. Extraction of chitosan from fragile fungal biomass is more easily done than the conventional process using less intensive processing steps. This could result in a higher profit margin for the commercial production of chitosan.

Preliminary investigations have identified a top chitosan producer fungal strain *Mucor* (Amylomyces) *rouxii* ATCC 24905 among five other test strains for growth and chitosan yield from soybean meal. Table 1 presents the characterization of soybean meal samples obtained from three different suppliers that were shown to have similar nutrient compositions with up to 36% carbohydrates and 48% proteins, making them excellent fermentation substrates. The bench-scale fermentation experiments involved 5-gram soy meal substrates in small petri dishes. Additional experiments will be aimed at optimizing conditions and scaling up the process using the selected fungal strain.

TABLE 1

Characterization of soybean meal samples for potential use as fermentation substrate.

| Results (% w/w) | ADM | Supplier CHS | Zeeland | Average |
|---|---|---|---|---|
| Carbohydrates | 36.50 | 36.65 | 34.77 | 35.97 ± 1.04 |
| Proteins | 47.42 | 46.69 | 48.37 | 47.49 ± 0.84 |
| Fat | 1.50 | 1.45 | 1.37 | 1.44 ± 0.07 |
| Moisture | 8.52 | 8.11 | 9.37 | 8.67 ± 0.64 |
| Ash | 6.06 | 7.10 | 6.12 | 6.43 ± 0.58 |

Example 2: Optimum Solid-State Fermentation and Extraction Conditions for Maximum Chitosan Production Experiments have been performed to determine the optimum solid-state fermentation and extraction conditions for maximum chitosan production (3.5-5% by weight of soy meal substrate) by the selected fungus *M. rouxii* ATCC 24905. These desired conditions suggest the appropriate length of fungal cultivation (6 days), initial moisture content (50%) and pH (unadjusted, 5.5) of the soybean meal substrate, incubation temperature (25° C.), and extraction method (Method 2—1 M NaOH at 121° C. for 20 min (10 mL per g of substrate) followed by 2% (v/v) acetic acid (10 mL per g of substrate) at 95° C. for 8 hours). The result of this optimization study is published in the Journal of Materials Science and Chemical Engineering (Volume 3, pp. 11-21) and is incorporated herein by reference in its entirety. These investigations also yielded an initial cost estimate of the fungal chitosan product from the bench-scale soy meal fermentation process and the benchmark best case price to be competitive the conventional paper barrier coating material it seeks to replace (i.e., phenolformaldehyde resins, $2-3 per pound). This analysis shows that the best-case scenario cost ($2.88) could be achieved via further process scale-up and optimization to achieve a 6-fold increase in the yield and 3- to 4-fold reduction in the use of chitosan extraction reagents.

Example 3: Semi-Pilot Scale Soy Meal Fermentation Tests

Semi-pilot scale soy meal fermentation tests were conducted for further optimization of the process. These results are summarized in Table 2 below. An average of 1.01% was obtained from the two semi-pilot trials. The Trial 1 result shows a decent chitosan yield but with a chitosan product that is visually similar to the commercially available chitosan while the Trial 2 product showed more of a clumped material. Further semi-pilot scale trials will be conducted to optimize process conditions and parameters specific to the tray fermentation system such as soy meal substrate depth, aeration rate, and incubation humidity. Further optimization of extraction conditions and procedures to minimize losses will also be conducted. The goal is to achieve an overall yield of at least 5% for one fermentation and extraction batch. Tests were also conducted to determine the suitability of recycling the spent fermented soy meal solids after chitosan extraction as additional substrate for fungal growth and chitosan production. No substantial growth of the test fungi was observed on this substrate presumably due to the expected lower nutrient levels. These tests suggest that the spent base used for substrate de-proteinization would likely contain substantial amounts of proteins that could used to reconstitute/rehydrate the spent solids prior to fungal inoculation. This could theoretically lead to improved fungal growth and reuse as carbon and nutrient source for additional chitosan production. Additional studies must be conducted to further improve the production efficiency and economics of chitosan production from soy meal using the direct solid-state fermentation approach.

TABLE 2

Results of semi pilot soy meal fermentation and extraction runs for fungal chitosan production

| Trial | Initial soymeal mass (g) | Losses (g) | Fungal chitosan recovered (g) | Yield (% w/w) |
|---|---|---|---|---|
| 1 | 595 | 37 | 6.43 | 1.15 |
| 2 | 600 | 2 | 5.20 | 0.87 |

Example 4: Chitosan Paperboard Coating for HVAC Applications

Concurrent investigations were conducted to test the applicability of fungal chitosan from soy meal fermentation as a functional paperboard barrier coating material. The intended application is to provide simultaneous wet stiffness, water absorption and evaporative cooling properties to paper-based corrugated cooling pads for HVAC (Heating, Ventilation, and Air Conditioning) applications in agricultural livestock enclosures. Current manufacturers use phenolic resin (phenolformaldehyde) coatings but their customers report premature structural failure and reduced evaporative cooling performance of the current products. Based on the reported properties and paper-related applications of chitosan in literature, it was hypothesized that chitosan will improve wet stiffness of the paper base sheets while simultaneously improving water absorption properties and evaporative cooling performance. The target critical-to-quality (CTQ) parameters and their specified levels are a wet stiffness of 1.6 gram-force and wicking height of 2 inches under standard TAPPI conditions.

The results of these investigations are summarized in FIGS. 5 and 6 below. In terms of wet stiffness, FIG. 5 shows that increasing the coat weight of commercial chitosan (using aqueous acetic acid carrier) showed no significant difference in the wet stiffness in both the machine direction (MD) and the cross direction (CD). Both treatments were not significantly different with an uncoated sheet in terms of wet stiffness but showed a generally higher trend. The use of fungal chitosan (coat weight of 3.5 g/m$^2$, aqueous acetic acid carrier) also showed no significant difference in terms of wet stiffness compared to commercial chitosan at 3.5 to 6.1 g/m$^2$ coat weights and uncoated sheets. However, a significantly higher wet stiffness was obtained when coating commercial chitosan (3.5 g/m$^2$ coat weight) using a methanol/aqueous acetic acid carrier, specifically in the machine direction. This chitosan coating carrier system was tested in order to render the chitosan-based coating material applicable for coating material delivery. All chitosan-coating conditions showed significantly higher wet stiffness than the phenolic resin-coated paper base sheets. In contrast, FIG. 6 shows a significantly higher water wicking height of up to 1.75 inches and water absorption mass gain of almost 50% for fungal chitosan-coated paper base sheets. Paper sheets coated with commercial chitosan dispersed in methanol/aqueous acetic acid carrier showed the lowest wicking height compared with all other chitosan coating conditions.

What is claimed is:

1. A composite fiber stock material comprising:
   at least one layer of a fibrous base sheet; and
   at least one chitosan layer comprising a chitosan coat weight from about 1 g/m$^2$ to about 10 g/m$^2$;
   wherein the composite fiber stock material has an air permeance from about 20 nm/Pa s to about 50 nm/Pa s.

2. The composite fiber stock material of claim 1, wherein the air permeance is from about 25 nm/Pa s to about 35 nm/Pa s.

3. The composite fiber stock material of claim 1, wherein the composite has a Cobb value from about 10 g/m$^2$ to about 50 g/m$^2$.

4. The composite fiber stock material of claim 1, wherein the composite material has a wet stiffness from about 1.0 gram-force to about 2.0 gram-force.

5. The composite fiber stock material of claim 1, wherein the composite material has a wet stiffness of about 1.6 gram-force.

6. The composite fiber stock material of claim 1, wherein the composite material has a wicking height of about 2 inches.

7. The composite fiber stock material of claim 1, wherein the at least one chitosan layer is derived from a fungal biomass in a solid-state fermentation of a soybean meal.

8. The composite fiber stock material of claim 1, wherein the at least one chitosan layer is derived from a biomass selected from the group consisting of: crustaceans; insects; mollusks; and fungi.

9. An evaporative cooling pad comprising:
   at least one layer of a fibrous base sheet; and
   at least one chitosan layer comprising a chitosan coat weight from about 1 g/m$^2$ to about 10 g/m$^2$;
   wherein the evaporative cooling pad has an air permeance from about 20 nm/Pa s to about 50 nm/Pa s.

10. The evaporative cooling pad of claim 9, wherein the evaporative cooling pad is used in a heating, ventilation, and air conditioning apparatus.

11. The evaporative cooling pad of claim 9, wherein the air permeance is from about 25 nm/Pa s to about 35 nm/Pa s.

12. The evaporative cooling pad of claim 9, wherein the composite has a Cobb value from about 10 g/m$^2$ to about 50 g/m$^2$.

13. The evaporative cooling pad of claim 9, wherein the composite material has a wet stiffness from about 1.0 gram-force to about 2.0 gram-force.

14. The evaporative cooling pad of claim 9, wherein the composite material has a wicking height of about 2 inches.

15. The evaporative cooling pad of claim 9, wherein the at least one chitosan layer is derived from a fungal biomass in a solid-state fermentation of a soybean meal.

16. The evaporative cooling pad of claim 9, wherein the at least one chitosan layer is derived from a biomass selected from the group consisting of: crustaceans; insects; mollusks; and fungi.

17. A method for making a composite fiber stock material comprising:
   forming at least one layer of a fiber stock;
   coupling at least one chitosan layer to the at least one layer of fiber stock using a chitosan solution comprising a methanol solvent and an acetic acid solvent to produce a composite fiber stock material having a chitosan coat weight with a chitosan thickness; and
   drying the composite fiber stock material at a controlled pressure and a controlled temperature for a period of time;
   wherein the composite fiber stock material has a chitosan coat weight from about 1 g/m$^2$ to about 10 g/m$^2$ and an air permeance from about 30 nm/Pa s to about 50 nm/Pa s.

18. The method of claim 17, wherein the composite fiber stock material has a Cobb value from about 10 g/m$^2$ to about 50 g/m$^2$.

19. The method of claim 17, wherein the composite fiber stock material has a wicking height of about 2 inches.

20. The method of claim 17, wherein the at least one chitosan layer is derived from a fungal biomass in a solid-state fermentation of a soybean meal.

* * * * *

UNITED STATES PATENT AND TRADEMARK OFFICE
CERTIFICATE OF CORRECTION

PATENT NO. : 9,982,393 B2  
APPLICATION NO. : 15/207021  
DATED : May 29, 2018  
INVENTOR(S) : Andro Hernandez Mondala et al.

Page 1 of 1

It is certified that error appears in the above-identified patent and that said Letters Patent is hereby corrected as shown below:

Column 8, Line 34:  
"7 /m²" should be — 7 g/m² —

Column 9, Line 21:  
After "can" insert -- be --

Column 14, Line 3:  
"is" should be — are —

Column 17, Line 61:  
After "competitive" insert -- with --

Signed and Sealed this  
Sixth Day of November, 2018

Andrei Iancu  
*Director of the United States Patent and Trademark Office*